(12) United States Patent
Wattebled et al.

(10) Patent No.: US 8,686,216 B2
(45) Date of Patent: *Apr. 1, 2014

(54) SUPERABSORBENT COMPOSITION WITH METAL SALICYLATE FOR ODOR CONTROL

(75) Inventors: Laurent Wattebled, Dusseldorf (DE); Franck Furno, Dusseldorf (DE)

(73) Assignee: Evonik Degussa GmbH, Essen (DE)

( * ) Notice: Subject to any disclaimer, the term of this patent is extended or adjusted under 35 U.S.C. 154(b) by 327 days.

This patent is subject to a terminal disclaimer.

(21) Appl. No.: 12/867,943

(22) PCT Filed: Feb. 27, 2009

(86) PCT No.: PCT/EP2009/052347
§ 371 (c)(1),
(2), (4) Date: Sep. 14, 2010

(87) PCT Pub. No.: WO2009/109524
PCT Pub. Date: Sep. 11, 2009

(65) Prior Publication Data
US 2011/0009272 A1     Jan. 13, 2011

(30) Foreign Application Priority Data
Mar. 5, 2008 (DE) .......... 10 2008 012 728

(51) Int. Cl.
| A61F 13/15 | (2006.01) |
| A61K 31/60 | (2006.01) |
| A61K 47/30 | (2006.01) |
| A61K 33/32 | (2006.01) |

(52) U.S. Cl.
USPC ........ 604/367; 604/358; 514/772.3; 514/159; 424/641

(58) Field of Classification Search
USPC ......... 604/367, 358; 514/159, 772.3; 424/641
See application file for complete search history.

(56) References Cited

U.S. PATENT DOCUMENTS

| 4,076,663 | A | 2/1978 | Masuda et al. |
| 4,131,576 | A | 12/1978 | Iovine et al. |
| 4,172,173 | A | 10/1979 | Trapasso et al. |
| 4,179,367 | A | 12/1979 | Barthell et al. |
| 4,286,082 | A | 8/1981 | Tsubakimoto et al. |
| 4,340,706 | A | 7/1982 | Obayashi et al. |
| 4,587,308 | A | 5/1986 | Makita et al. |
| 4,766,173 | A | 8/1988 | Bailey et al. |
| 4,857,610 | A | 8/1989 | Chmelir et al. |
| 4,893,999 | A | 1/1990 | Chmelir et al. |
| 5,045,322 | A | 9/1991 | Blake et al. |
| 5,409,771 | A | 4/1995 | Dahmen et al. |
| 5,610,220 | A | 3/1997 | Klimmek et al. |
| 5,672,633 | A | 9/1997 | Brehm et al. |
| 5,712,316 | A | 1/1998 | Dahmen et al. |
| 6,060,557 | A | 5/2000 | Dahmen et al. |
| 6,403,700 | B1 | 6/2002 | Dahmen et al. |
| 6,579,958 | B2 * | 6/2003 | Wilson .......... 526/185 |
| 6,605,673 | B1 | 8/2003 | Mertens et al. |
| 6,620,889 | B1 | 9/2003 | Mertens et al. |
| 6,623,848 | B2 | 9/2003 | Brehm et al. |
| 6,720,073 | B2 * | 4/2004 | Lange et al. .......... 428/403 |
| 6,831,142 | B2 | 12/2004 | Mertens et al. |
| 6,911,572 | B1 | 6/2005 | Bruhn et al. |
| 6,916,465 | B2 | 7/2005 | Panzer et al. |
| 6,958,429 | B2 | 10/2005 | Bruhn et al. |

(Continued)

FOREIGN PATENT DOCUMENTS

| DE | 2612846 | 2/1978 |
| DE | 2706135 A1 | 8/1978 |

(Continued)

OTHER PUBLICATIONS

F.L. Buchholz, "Absorbency and Superabsorbency," Chapter 1, Modern Superabsorbent Polymer Technology, Copyright 1998, pp. 1-17, Wiley-VCH, New York.

(Continued)

*Primary Examiner* — Abigail Fisher
(74) *Attorney, Agent, or Firm* — Smith Moore Leatherwood LLP; Philip P. McCann; John P. Zimmer

(57) ABSTRACT

The present invention relates to a water-absorbing particulate composition comprising water-absorbing polymer particulate structure comprising partly neutralized, crosslinked polyacrylate, a surface crosslinking agent and a compound of the structure I

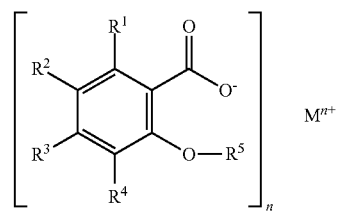

in which $R^1$, $R^2$, $R^3$ and $R^4$ can be identical or different and in each case represent a hydrogen atom, a halogen atom, a $C_1$- to $C_4$-hydrocarbon group or a hydroxyl group, $R^5$ represents a hydrogen atom, a $C_1$- to $C_4$-hydrocarbon group or an acetyl group, n represents an integer chosen from the group consisting of 1, 2 or 3 and $M^{n+}$ represents an n-valent metal cation or an $H^+$ cation. In addition, the present invention also relates to a process for the preparation of a water-absorbing composition, the water-absorbing composition obtainable by this process, a composite, a process for the production of a composite, the composite obtainable by this process, and products, such as hygiene articles.

13 Claims, 1 Drawing Sheet

(56) References Cited

U.S. PATENT DOCUMENTS

| | | |
|---|---|---|
| 7,144,957 B2 | 12/2006 | Funk et al. |
| 7,179,862 B2 | 2/2007 | Mertens et al. |
| 7,226,584 B2 | 6/2007 | Lersch et al. |
| 7,285,599 B2 | 10/2007 | Mertens et al. |
| 7,541,395 B2 | 6/2009 | Reimann et al. |
| 7,572,864 B2 | 8/2009 | Mertens et al. |
| 7,625,957 B2 | 12/2009 | Harren et al. |
| 7,728,079 B2 | 6/2010 | Harren et al. |
| 2003/0135172 A1 | 7/2003 | Whitmore et al. |
| 2003/0207997 A1 | 11/2003 | Mertens et al. |
| 2004/0024374 A1 | 2/2004 | Hjorth et al. |
| 2005/0171235 A1 | 8/2005 | Harren et al. |
| 2006/0029567 A1 | 2/2006 | Dutkiewicz |
| 2006/0029782 A1 | 2/2006 | Harren et al. |
| 2006/0057389 A1 | 3/2006 | Reimann et al. |
| 2007/0015860 A1 | 1/2007 | Frank |
| 2007/0066754 A1 | 3/2007 | Loeker et al. |
| 2007/0129495 A1 | 6/2007 | Mertens et al. |
| 2007/0260357 A1 | 11/2007 | Issberner et al. |
| 2008/0029039 A1* | 2/2008 | Jenkins .................. 119/173 |
| 2008/0221277 A1 | 9/2008 | Walden et al. |
| 2008/0280128 A1 | 11/2008 | Furno et al. |
| 2009/0023006 A1 | 1/2009 | Bub et al. |
| 2009/0105389 A1 | 4/2009 | Walden et al. |
| 2009/0130040 A1 | 5/2009 | Jonchiere |
| 2009/0134357 A1 | 5/2009 | Bub et al. |
| 2009/0202805 A1 | 8/2009 | Furno et al. |
| 2009/0209683 A1 | 8/2009 | Reimann et al. |
| 2009/0227741 A1 | 9/2009 | Walden et al. |
| 2009/0239995 A1 | 9/2009 | Bub et al. |
| 2010/0035757 A1 | 2/2010 | Furno et al. |
| 2010/0036004 A1 | 2/2010 | Harren et al. |
| 2010/0057027 A1 | 3/2010 | Furno et al. |
| 2010/0099799 A1 | 4/2010 | Fricker et al. |
| 2010/0105808 A1 | 4/2010 | Fricker et al. |
| 2010/0105809 A1 | 4/2010 | Fricker et al. |
| 2010/0119830 A1 | 5/2010 | Braig et al. |
| 2010/0209379 A1* | 8/2010 | Furno et al. .................. 424/76.6 |

FOREIGN PATENT DOCUMENTS

| | | |
|---|---|---|
| DE | 2840010 A1 | 6/1979 |
| DE | 3503458 A1 | 8/1985 |
| DE | 3544770 | 6/1987 |
| DE | 3713601 | 11/1988 |
| DE | 3816252 A1 | 11/1988 |
| DE | 4020780 C1 | 8/1991 |
| DE | 4244548 A1 | 7/1994 |
| DE | 4418818 A1 | 1/1995 |
| DE | 4333056 A1 | 3/1995 |
| DE | 19518645 C1 | 9/1996 |
| DE | 19529348 A1 | 2/1997 |
| DE | 19825486 A1 | 2/2000 |
| DE | 19909653 A1 | 9/2000 |
| DE | 19909838 A1 | 9/2000 |
| DE | 19939662 A1 | 2/2001 |
| DE | 10160933 A1 | 6/2003 |
| DE | 10334271 A1 | 2/2005 |
| DE | 102005055497 A1 | 5/2007 |
| EP | 0532002 | 3/1993 |
| EP | 0889063 A1 | 1/1999 |
| EP | 1358894 A1 | 11/2003 |
| JP | 60158861 | 1/1984 |
| WO | 9605234 A1 | 2/1996 |
| WO | 9631644 A1 | 10/1996 |
| WO | 9934843 A1 | 7/1999 |
| WO | 0071176 A1 | 11/2000 |
| WO | 0130748 A1 | 5/2001 |
| WO | 0170191 A1 | 9/2001 |
| WO | 0170210 A2 | 9/2001 |
| WO | 02056812 A2 | 7/2002 |
| WO | 03028778 A2 | 4/2003 |
| WO | 2004037903 A2 | 5/2004 |
| WO | 2005011860 A2 | 2/2005 |
| WO | 2007057043 A1 | 5/2007 |
| WO | 2007057203 A2 | 5/2007 |
| WO | 2007122343 A1 | 11/2007 |
| WO | 2010052182 A1 | 5/2010 |

OTHER PUBLICATIONS

English translation of International Preliminary Report on Patentability completed on Aug. 7, 2008 in PCT/EP2006/011055.

Furno et al., U.S. Appl. No. 12/679,631, filed Mar. 23, 2010.

German language International Search Report mailed on Aug. 13, 2010 in PCT/EP2008/008081.

German language Written Opinion mailed on Aug. 13, 2010 in PCT/EP2008/008081.

German language Written Opinion mailed on Jun. 12, 2009 in PCT/EP2009/052347.

Harren et al., U.S. Appl. No. 12/600,964, filed Dec. 15, 2009.

International Search Report mailed on Jun. 12, 2009 in PCT/EP2009/052347.

International Search Report mailed on Oct. 26, 2007 in PCT/EP2006/011055.

* cited by examiner

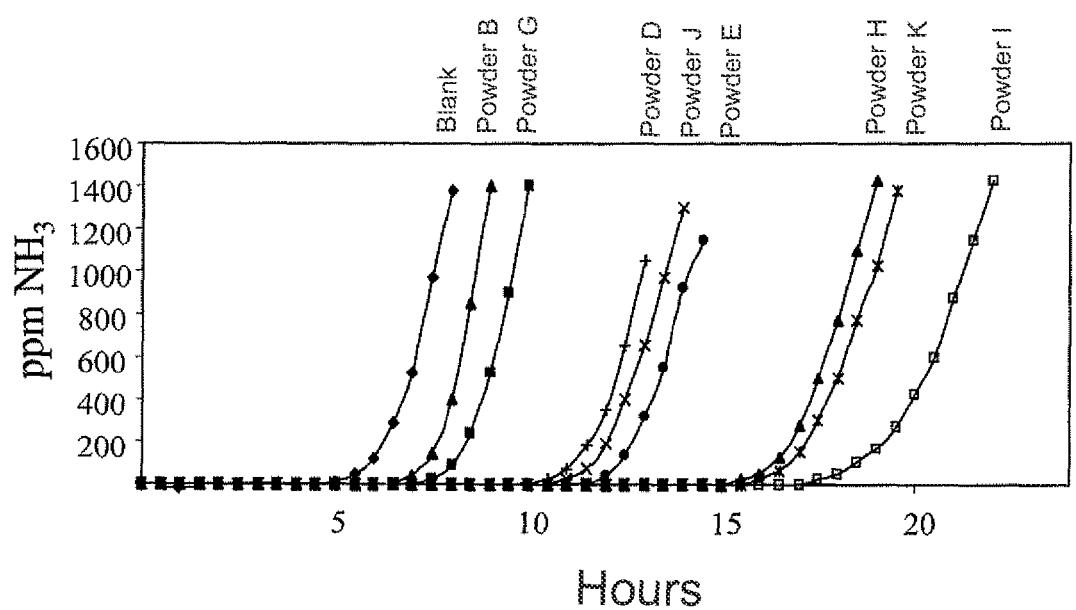

SUPERABSORBENT COMPOSITION WITH METAL SALICYLATE FOR ODOR CONTROL

This application is a national stage application under 35 U.S.C. 371 of International Application No. PCT/EP2009/052347 filed 27 Feb. 2009, which claims priority to German Application No. DE 10 2008 012 728.0 filed 5 Mar. 2008, the disclosures of which are expressly incorporated herein by reference.

The present invention relates to a water-absorbing composition, a process for the preparation of a water-absorbing composition, the water-absorbing composition obtainable by this process, a composite, a process for the production of a composite, the composite obtainable by this process, chemical products, such as, for example, hygiene articles, the use of a water-absorbing composition or of a composite and the use of a defined compound.

BACKGROUND

Superabsorbers are water-insoluble crosslinked polymers which are capable of absorbing and retaining under pressure large amounts of aqueous liquids, in particular body fluids, preferably urine or blood, with swelling and formation of hydrogels. In general, these uptakes of liquid are an amount of water at least 10 times or even at least 100 times the dry weight of the superabsorbers or superabsorbent compositions. Due to these characteristic properties, these polymers are mainly used in sanitary articles, such as baby nappies, incontinence products or sanitary towels. A comprehensive overview of superabsorbers and superabsorbent compositions, their use and their preparation is given by F. L. Buchholz and A. T. Graham (editors) in "*Modern Superabsorbent Polymer Technology*", Wiley-VCH, New York, 1998.

Superabsorbers are as a rule prepared by free radical polymerization of usually partly neutralized monomers carrying acid groups in the presence of crosslinking agents. In this context, polymers having different absorption properties can be prepared, according to the choice of the monomer composition, the crosslinking agents as well as the polymerization conditions and the processing conditions for the hydrogel obtained after the polymerization. Further possibilities are offered by the preparation of graft polymers, for example using chemically modified starch, cellulose and polyvinyl alcohol in accordance with DE-OS 26 12 846.

DE 40 20 780 C1 discloses the after-treatment of superabsorbent polymers by post-crosslinking of the surfaces of the polymer particles. By the post-crosslinking of the surface of the water-absorbing polymer particles, the absorption capacity of the polymer particles under the action of pressures is increased in particular.

DE 199 09 653 A1 and DE 199 09 838 A1 describe pulverulent polymers which are post-crosslinked on the surface and absorb water, aqueous or serous liquids or blood, and which are based on monomers carrying acid groups and have been coated with a surface post-crosslinking agent and a cation in aqueous solution and post-crosslinked. The polymers disclosed in this prior art have advantageous absorption properties compared with conventional polymers, in particular a high permeability.

During more prolonged wearing of hygiene articles which contain absorbent polymers and which have already partly absorbed body fluids, such as urine, or during storage of used nappies, such as is usual, for example, in hospitals, an unpleasant odor nuisance may immediately occur due to the organic constituents of the urine and the body heat of the person wearing the article. To counteract this, numerous attempts have been made to achieve binding of the odor-forming substances by appropriate admixtures in the constituents of the hygiene article other than the superabsorber, or to cover up the odor by perfumes or the like. The introduction of such substances in the form of constituents other than superabsorbers often has a negative effect on the performance of these hygiene articles during wearing. Thus, the odor-inhibiting or odor-reducing substances which are initially present spatially separated from the superabsorber region are often introduced by the body fluids into the superabsorber-containing region of a hygiene article, for example by washing in, where they then have a negative effect on the performance of the superabsorber and therefore of the hygiene article overall. A further disadvantage of this concept is that the majority of the body fluid released into the hygiene article is in any case in the superabsorber, and the odor-inhibiting or odor-reducing substances outside the superabsorber can display their action less efficiently.

DE 198 25 486 A1 and DE 199 39 662 A1 disclose the combination of superabsorbers with cyclodextrin for reducing odor. However, it is to be seen from this highly promising approach that the cyclodextrin shows its odor-inhibiting action in the superabsorber only under certain conditions, namely when it is ensured that the cyclodextrin does not separate again from the superabsorber. It is preferable here for the cyclodextrin to be incorporated at least into the surface of the superabsorber article by the cyclodextrin and/or cyclodextrin derivatives being covalently and/or ionically bonded and/or enclosed therein.

DE 103 34 271 A1 furthermore discloses superabsorber agglomerates which can contain a large number of odor-binding substances homogeneously in the agglomerate. However, this specification, which discloses an outstanding solution for the use of superabsorber fine particles, provides no superabsorbers having odor-binding properties which are particularly suitable for use in hygiene articles. Thus, in addition to an efficient and effective use of the odor-binding substances, the superabsorber properties influenced by these odor-binding substances are still in need of improvement.

DE 10 2005 055 497 A1 teaches that superabsorbent polymers are provided with improved odor-binding properties by bringing them into contact with metal salts of ricinoleic acid, optionally in combination with amino acids to improve solubility.

In general, the present invention was based on the object of moderating or even overcoming the disadvantages emerging from the prior art.

SUMMARY

The present invention includes various embodiments as set forth herein.

FIGURE

The foregoing and other features, aspects, and advantages of the present invention will become better understood with regard to the following description, appended claims, and accompanying drawing where:

FIG. 1 is a graph showing the odor-binding effect of zinc salicylate in a superabsorber.

One object according to the invention was in particular to provide a water-absorbing composition which comprises a superabsorber and an odor-binding additive and which has good odor-binding properties. In addition to the advantageous odor-binding property, the water-absorbing composition should also be distinguished by a good performance in a hygiene article. In particular, the performance of a hygiene article which contains this water-absorbing composition should be essentially equally as good as or even better than the performance of the hygiene article with a superabsorber which does not contain the odor-binding additive.

Furthermore, in particular the flow rate of the water-absorbing composition should as far as possible not be influenced at all or should at most be influenced slightly by the use of the odor-binding additive, so that the water-absorbing composition can be conveyed and processed more easily compared with the compositions known from the prior art which comprise an odor-binding additive. The permeability of the water-absorbing composition to aqueous liquids should moreover be at least comparable, but advantageously improved further compared with the odor-binding water-absorbing compositions known from the prior art.

The amount of odor-binding additive contained in the water-absorbing composition should also be reduced as far as possible, for the same odor-binding capacity, compared with the odor-binding water-absorbing compositions known from the prior art.

An object according to the invention was furthermore to provide a process with which such a water-absorbing composition can be obtained.

An object according to the invention was moreover to provide a hygiene article which, in addition to good odor-binding properties, also shows a good performance.

The present invention was additionally based on the object of providing water-absorbing compositions which can generally be incorporated into composites or can also be used as a composite or as such in chemical products or constituents thereof.

DETAILED DESCRIPTION

A contribution towards achieving the abovementioned objects is made by a water-absorbing composition comprising water-absorbing polymer structures and a compound of the structure I

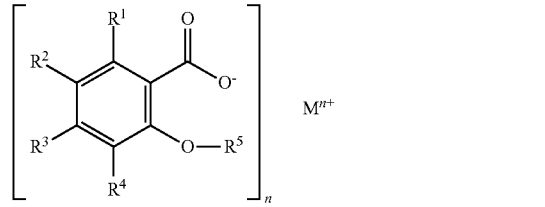

structure I in which
R$^1$, R$^2$, R$^3$ and R$^4$ can be identical or different and in each case represent a hydrogen atom, a halogen atom, for example a chlorine atom or a bromine atom, a C$_1$- to C$_4$-hydrocarbon group, preferably a methyl group or an ethyl group, particularly preferably a methyl group, or a hydroxyl group,
R$^5$ represents a hydrogen atom, a C$_1$- to C$_4$-hydrocarbon group or an acetyl group, preferably a hydrogen atom or an acetyl group and most preferably a hydrogen atom,
n represents an integer chosen from the group consisting of 1, 2 or 3, particularly preferably the number 1 or the number 2 and most preferably the number 2, and
M$^{n+}$ represents an n-valent metal cation or an H$^+$ cation, preferably an H$^+$ cation, a monovalent metal cation of an alkali metal or a divalent metal cation of an alkaline earth metal or of a transition metal, particularly preferably an H$^+$ cation, an Na$^+$ cation or a divalent metal cation of a transition metal of groups 10, 11 or 12, particularly preferably of group 12 and most preferably a Zn$^{2+}$ cation.

According to a particularly preferred embodiment of the water-absorbing composition according to the invention, this comprises a compound of the structure I in which R$^1$, R$^2$, R$^3$, R$^4$ and R$^5$ represent a hydrogen atom. According to this particular embodiment of the composition according to the invention, the compound of the structure I is salicylic acid (n=1, M$^+$=H$^+$), sodium salicylate (n=1, M$^+$=Na$^+$) or zinc salicylate (n=2, M$^{2+}$=Zn$^{2+}$), wherein zinc salicylate is most preferred as the compound of the structure I.

It is also preferable according to the invention for the water-absorbing composition to contain the compound of the structure I in an amount in a range of from 0.001 to 10 wt. %, particularly preferably in a range of from 0.05 to 5 wt. % and most preferably in an amount in a range of from 0.1 to 3 wt. %, in each case based on the total weight of the water-absorbing polymer structures.

It is furthermore preferable according to the invention for the water-absorbing composition according to the invention to contain the compound of the structure I in the form of a powder and consequently in the form of small particles, it furthermore being preferable for such a powder to comprise at most 25 wt. %, still more preferably at most 10 wt. %, moreover preferably at most 5 wt. %, in each case based on the total weight of the compound of the structure I, but most preferably no preferably individual particles which are greater than 700 µm, particularly preferably greater than 500 µm and most preferably greater than 300 µm in diameter. However, it is entirely possible for the powder of the compound I also to contain agglomerates of at least two particles which are greater than 700 µm, 500 µm or 300 µm, it being entirely possible for the amount of these agglomerates also to be greater than 25 wt. %, 10 wt. % or 5 wt. %. In particular, it may prove advantageous if the powder of the compound of the structure I is based to the extent of at least 50 wt. %, still more preferably to the extent of at least 90 wt. % and most preferably exclusively on particles having a diameter in a range of from 50 to 800 µm, particularly preferably 50 to 500 µm and most preferably 50 to 350 µm.

It is furthermore preferable according to the invention for the powder particles of the compound of the structure I to be immobilized on the surface of the water-absorbing polymer structures via a binder, it being possible in principle for organic or inorganic binders to be employed as the binder. Possible binders in this context are, in particular, thermoplastic hot melt adhesives, hydrophilic, preferably water-soluble polymers or also water itself. Thermoplastic hot melt adhesives which can be employed in this context are in particular those particulate compounds which are mentioned as thermoplastic adhesives in WO-A-2005/011860. Hydrophilic, preferably water-soluble polymers which can be employed are, in particular, polyvinyl alcohols, which can be obtained by partial or complete hydrolysis of polyvinyl acetate, or polyalkylene glycols, in particular polyethylene glycols having a molecular weight in a range of from 1,000 to 50,000 g/mol, particularly preferably in a range of from 1,500 to 25,000 g/mol and most preferably in a range of from 2,000 to 15,000 g/mol.

The water-absorbing polymer structures contained in the composition according to the invention are preferably based on partly neutralized crosslinked polyacrylates.

In this context, water-absorbing polymer structures which are preferred according to the invention are, in particular, fibers, foams or particles, fibers and particles being particularly preferred and particles being most preferred.

Polymer fibers which are preferred according to the invention have dimensions such that they can be incorporated as yarns for textiles and also directly into textiles. It is preferable according to the invention for the polymer fibers to have a length in the range of from 1 to 500 mm, preferably 2 to 500 mm and particularly preferably 5 to 100 mm and a diameter in the range of from 1 to 200 denier, preferably 3 to 100 denier and particularly preferably 5 to 60 denier.

Polymer particles which are preferred according to the invention have dimensions such that they have an average particle size according to ERT 420.2-02 in the range of from 10 to 3,000 µm, preferably 20 to 2,000 µm and particularly preferably 150 to 850 µm or 150 to 600 µm. In this context it is particularly preferable for the content of polymer particles having a particle size in a range of from 300 to 600 µm to be at least 30 wt. %, particularly preferably at least 40 wt. %, moreover preferably at least 50 wt. % and most preferably at least 75 wt. %, based on the total weight of the water-absorbing polymer particles. According to another embodiment of the water-absorbing polymer structures according to the invention, the content of polymer particles having a particle size in a range of from 150 to 850 µm is at least 50 wt. %, particularly preferably at least 75 wt. %, moreover preferably at least 90 wt. % and most preferably at least 95 wt. %, based on the total weight of the water-absorbing polymer particles.

In a preferred embodiment of the water-absorbing polymer structures contained in the water-absorbing composition according to the invention, these are based on (α1) 20-99.999 wt. %, preferably 55-98.99 wt. % and particularly preferably 70-98.79 wt. % of polymerized ethylenically unsaturated monomers carrying acid groups or salts thereof or polymerized ethylenically unsaturated monomers containing a protonated or quaternized nitrogen, or mixtures thereof, mixtures containing at least ethylenically unsaturated monomers containing acid groups, preferably acrylic acid, being particularly preferred, (α2) 0-80 wt. %, preferably 0-44.99 wt. % and particularly preferably 0.1-44.89 wt. % of polymerized monoethylenically unsaturated monomers which can be copolymerized with (α1), (α3) 0.001-5 wt. %, preferably 0.01-3 wt. % and particularly preferably 0.01-2.5 wt. % of one or more crosslinking agents, (α4) 0-30 wt. %, preferably 0-5 wt. % and particularly preferably 0.1-5 wt. % of a water-soluble polymer, (α5) 0-20 wt. %, preferably 2.5-15 wt. % and particularly preferably 5-10 wt. % of water, and (α6) 0-20 wt. %, preferably 0-10 wt. % and particularly preferably 0.1-8 wt. % of one or more auxiliary substances, the sum of the amounts by weight of (α1) to (α6) being 100 wt. %.

The monoethylenically unsaturated monomers (α1) containing acid groups can be partly or completely, preferably partly neutralized. Preferably, the monoethylenically unsaturated monomers containing acid groups are neutralized to the extent of at least 25 mol %, particularly preferably to the extent of at least 50 mol % and moreover preferably to the extent of 50-80 mol %. According to particular embodiments of the composition according to the invention, however, this comprises water-absorbing polymer structures which are neutralized to the extent of at most 78 mol %, particularly preferably to the extent of at most 70 mol % and to the extent of at least 50 mol %. In this connection, according to one embodiment of the composition according to the invention, the degree of neutralization of the water-absorbing polymer structures can be in a range of from 65 to 80 mol %, particularly preferably in a range of from 70 to 78 mol %, and according to another embodiment in a range of from 45 to 65 mol %, particularly preferably in a range of from 50 to 60 mol %. Reference is furthermore made to DE 195 29 348 A1, the disclosure of which is introduced herewith as reference. The neutralization can also be carried out partly or completely after the polymerization. The neutralization can furthermore be carried out with alkali metal hydroxides, alkaline earth metal hydroxides, ammonia and carbonates and bicarbonates. In addition, any further base which forms a water-soluble salt with the acid is conceivable. A mixed neutralization with various bases is also conceivable. Neutralization with ammonia and alkali metal hydroxides is preferred, particularly preferably with sodium hydroxide and with ammonia.

Furthermore, the free acid groups can predominate in a polymer, so that this polymer has a pH in the acidic range. This acidic water-absorbing polymer can be at least partly neutralized by a polymer having free basic groups, preferably amine groups, which is basic compared with the acidic polymer. These polymers are called "mixed-bed ion exchange absorbent polymers" (MBIEA polymers) in the literature and are disclosed, inter alia, in WO 99/34843 A1. The disclosure of WO 99/34843 A1 is introduced herewith as reference and thus forms part of the disclosure. As a rule, MBIEA polymers are a composition which comprises on the one hand basic polymers which are capable of exchanging anions, and on the other hand a polymer which is acidic compared with the basic polymer and is capable of exchanging cations. The basic polymer contains basic groups and is typically obtained by polymerization of monomers which carry basic groups or groups which can be converted into basic groups. These monomers are above all those which contain primary, secondary or tertiary amines or the corresponding phosphines or at least two of the above functional groups. This group of monomers includes, in particular, ethyleneamine, allylamine, diallylamine, 4-aminobutene, alkyloxycyclins, vinylformamide, 5-aminopentene, carbodiimide, formaldacin, melamine and the like, and secondary or tertiary amine derivatives thereof.

Preferred ethylenically unsaturated monomers (α1) containing acid groups are preferably those compounds which are mentioned as ethylenically unsaturated monomers (α1) containing acid groups in WO 2004/037903 A2, which is introduced as reference and thus forms part of the disclosure. Particularly preferred ethylenically unsaturated monomers (α1) containing acid groups are acrylic acid and methacrylic acid, acrylic acid being most preferred.

According to one embodiment of the process according to the invention, water-absorbing polymer structures in which the monoethylenically unsaturated monomers (α2) which can be copolymerized with (α1) are acrylamides, methacrylamides or vinylamides are employed.

Preferred (meth)acrylamides are, in addition to acrylamide and methacrylamide, alkyl-substituted (meth)acrylamides or aminoalkyl-substituted derivatives of (meth)acrylamide, such as N-methylol(meth)acrylamide, N,N-dimethylamino (meth)acrylamide, dimethyl(meth)acrylamide or diethyl (meth)acrylamide. Possible vinylamides are, for example, N-vinylamides, N-vinylformamides, N-vinylacetamides, N-vinyl-N-methylacetamides, N-vinyl-N-methylformamides and vinylpyrrolidone. Among these monomers, acrylamide is particularly preferred.

The monoethylenically unsaturated monomers (α2) which can be copolymerized with (α1) can also be water-soluble monomers. In this connection, alkoxypolyalkylene oxide (meth)acrylates, such as methoxypolyethylene glycol (meth)acrylates, are preferred in particular.

Water-dispersible monomers are furthermore preferred as monoethylenically unsaturated monomers (α2) which can be copolymerized with (α1). Water-dispersible monomers are acrylic acid esters and methacrylic acid esters, such as methyl (meth)acrylate, ethyl(meth)acrylate, propyl(meth)acrylate or butyl(meth)acrylate.

The monoethylenically unsaturated monomers (α2) which can be copolymerized with (α1) furthermore include methylpolyethylene glycol allyl ether, vinyl acetate, styrene and isobutylene.

Crosslinking agents (α3) which are preferably employed are those compounds which are mentioned as crosslinking agents (α3) in WO 2004/037903 A2. Among these crosslinking agents, water-soluble crosslinking agents are particularly preferred. In this context, N,N'-methylenebisacrylamide, polyethylene glycol di(meth)acrylates, triallylmethylammonium chloride, tetraallylammonium chloride and allylnonaethylene glycol acrylate prepared with 9 mol of ethylene oxide per mol of acrylic acid are most preferred.

The water-absorbing polymer structures can contain as water-soluble polymers (α4) water-soluble polymers such as partly or completely hydrolysed polyvinyl alcohol, polyvinylpyrrolidone, starch or starch derivatives, polyglycols or polyacrylic acid, preferably in a polymerized-in form. The molecular weight of these polymers is not critical, as long as they are water-soluble. Preferred water-soluble polymers are starch or starch derivatives or polyvinyl alcohol. The water-soluble polymers, preferably synthetic polymers, such as polyvinyl alcohol, can also serve as a graft base for the monomers to be polymerized.

Auxiliaries (α6) which are contained in the polymer structures are, preferably, standardizing agents, odor-binding agents, surface-active agents or antioxidants and those additives which have been employed for the preparation of the polymer structures (initiators etc.).

In a particular embodiment of the water-absorbing polymer structures contained in the water-absorbing composition according to the invention, these are based to the extent of at least 50 wt. %, preferably to the extent of at least 70 wt. % and moreover preferably to the extent of at least 90 wt. % on monomers which carry carboxylate groups. It is furthermore preferable according to the invention for component (α1) to be neutralized to the extent of at least 50 wt. %, it being possible according to one embodiment of the process according to the invention for the degree of neutralization of the water-absorbing polymer structures to be in a range of from 65 to 80 mol %, particularly preferably in a range of from 70 to 78 mol % and according to another embodiment in a range of from 45 to 65 mol %, particularly preferably in a range of from 50 to 60 mol %.

According to a preferred embodiment of the composition according to the invention, it is furthermore preferable for the water-absorbing polymer structures to have an inner region and an outer region surrounding the inner region, the outer region having a higher degree of crosslinking than the inner region. Such an inhomogeneous degree of crosslinking can be achieved by the water-absorbing polymer structures being post-crosslinked by coating with a suitable surface postcrosslinking agent which contains at least two functional groups which can react with the functional groups in the outer region of the water-absorbing polymer structure.

It is furthermore preferable according to the invention for the water-absorbing composition to be obtainable by bringing the water-absorbing polymer structures into contact with the compound of the structure I, it being particularly preferable for the compound of the structure I to be brought into contact with the water-absorbing polymer structures in an amount in a range of from 0.01 to 10 wt. %, particularly preferably in an amount in a range of from 0.05 to 5 wt. % and most preferably in an amount in a range of from 0.1 to 3 wt. %, in each case based on the total weight of the water-absorbing polymer structures. In this context, the bringing into contact is preferably brought about by simple mixing of the compound of the structure I with the water-absorbing polymer structures, optionally in the presence of the abovementioned binder.

A contribution towards achieving the abovementioned objects is also made by a process for the preparation of a water-absorbing composition comprising the process steps:
i) provision of a water-absorbing polymer structure;
ii) post-crosslinking of the water-absorbing polymer structure;
ii) bringing into contact of the water-absorbing polymer structure with a compound of the structure I

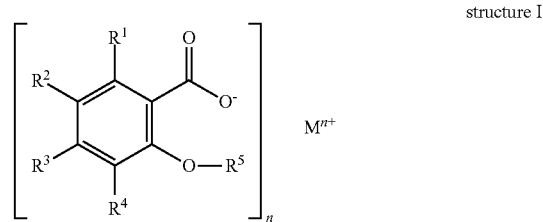

structure I in which
R$^1$, R$^2$, R$^3$ and R$^4$ can be identical or different and in each case represent a hydrogen atom, a halogen atom, for example a chlorine atom or a bromine atom, a C$_1$- to C$_4$-hydrocarbon group, preferably a methyl group or an ethyl group, particularly preferably a methyl group, or a hydroxyl group,
R$^5$ represents a hydrogen atom, a C$_1$- to C$_4$-hydrocarbon group or an acetyl group, preferably a hydrogen atom or an acetyl group and most preferably a hydrogen atom,
n represents an integer chosen from the group consisting of 1, 2 or 3, particularly preferably the number 1 or the number 2 and most preferably the number 2,
and
M$^{n+}$ represents an n-valent metal cation or an H$^+$ cation, preferably an H$^+$ cation, a monovalent metal cation of an alkali metal or a divalent metal cation of an alkaline earth metal or of a transition metal, particularly preferably an H$^+$ cation, an Na$^+$ cation or a divalent metal cation of a transition metal of groups 10, 11 or 12, particularly preferably of group 12 and most preferably a Zn$^{2+}$ cation,
wherein process step iii) can be carried out before, during or after process step ii), but is preferably carried out after process step ii) (which means that water-absorbing polymer structures which have already been post-crosslinked on the surface are brought into contact with the compound of the structure I).

Water-absorbing polymer structures are first provided in process step i) of the process according to the invention.

In this context, water-absorbing polymer structures provided in process step i) are preferably polymers which have been obtained by a process including the process steps:
a) free radical polymerization of ethylenically unsaturated, optionally partly neutralized monomers carrying acid groups in the presence of a crosslinking agent to form a hydrogel;

b) optionally comminution of the hydrogel;
c) at least partial drying of the optionally comminuted hydrogel to give water-absorbing polymer structures;
d) optionally grinding of the absorbent polymer structure obtained in this way and sieving off to a desired particle size fraction;
e) optionally further surface modifications of the water-absorbing polymer structures obtained in this way.

The free radical polymerization which is carried out in process step a) is preferably carried out in aqueous solution, where this aqueous solution preferably contains, in addition to water as the solvent, ($\alpha$1) the ethylenically unsaturated monomers carrying acid groups or salts thereof, acrylic acid being particularly preferred as the monomer carrying acid groups,
($\alpha$2) optionally monoethylenically unsaturated monomers which can be copolymerized with ($\alpha$1),
($\alpha$3) the crosslinking agent,
($\alpha$4) optionally a water-soluble polymer, and
($\alpha$6) optionally one or more auxiliaries.

Preferred monoethylenically unsaturated monomers which can be copolymerized with ($\alpha$1), water-soluble polymers and auxiliaries are in turn those compounds which have already been mentioned above as monomers which can be copolymerized with ($\alpha$1), as water-soluble polymers and as auxiliaries in connection with the water-absorbing polymer structures contained in the composition according to the invention.

The water-absorbing polymer structures can be prepared from the abovementioned monomers, comonomers, crosslinking agents, water-soluble polymers and auxiliary substances by various polymerization methods. There may be mentioned by way of example in this connection bulk polymerization, which is preferably carried out in kneading reactors, such as extruders, solution polymerization, spray polymerization, inverse emulsion polymerization and inverse suspension polymerization.

The solution polymerization is preferably carried out in water as the solvent. The solution polymerization can be carried out continuously or discontinuously. A broad spectrum of possibilities of variation with respect to the reaction circumstances, such as temperatures, nature and amount of the initiators and also of the reaction solution, is to be found from the prior art. Typical processes are described in the following patent specifications: U.S. Pat. No. 4,286,082, DE 27 06 135, U.S. Pat. No. 4,076,663, DE 35 03 458, DE 40 20 780, DE 42 44 548, DE 43 23 001, DE 43 33 056, DE 44 18 818. The disclosures are introduced herewith as reference and therefore form part of the disclosure.

The polymerization is initiated by an initiator as is generally conventional. Initiators which can be used for initiation of the polymerization are all the initiators which form free radicals under the polymerization conditions and are conventionally employed in the preparation of superabsorbers. Initiation of the polymerization by the action of electron beams on the polymerizable aqueous mixture is also possible. Nevertheless, the polymerization can also be initiated in the absence of initiators of the abovementioned type by the action of high-energy radiation in the presence of photoinitiators. Polymerization initiators can be contained in a solution of monomers according to the invention in dissolved or dispersed form. Possible initiators are all the compounds known to the person skilled in the art which dissociate into free radicals. These include, in particular, those initiators which have already been mentioned as possible initiators in WO 2004/037903 A2.

A redox system comprising hydrogen peroxide, sodium peroxodisulphate and ascorbic acid is particularly preferably employed for preparation of the water-absorbing polymer structures.

Inverse suspension and emulsion polymerization can also be used for preparation of the polymer structures. According to these processes, an aqueous, partly neutralized solution of monomers ($\alpha$1) and ($\alpha$2), optionally containing water-soluble polymers and auxiliary substances, is dispersed in a hydrophobic organic solvent with the aid of protective colloids and/or emulsifiers and the polymerization is started by free radical initiators. The crosslinking agents either are dissolved in the monomer solution and are metered together with this, or are added separately and optionally during the polymerization. The addition of a water-soluble polymer ($\alpha$4) as a graft base is optionally carried out via the monomer solution or by direct initial introduction into the oily phase. The water is then removed azeotropically from the mixture and the polymer is filtered off.

Both in the case of solution polymerization and in the case of inverse suspension and emulsion polymerization, the crosslinking can furthermore be carried out by polymerizing in the polyfunctional crosslinking agent dissolved in the monomer solution and/or by reaction of suitable crosslinking agents with functional groups of the polymer during the polymerization steps. The processes are described, for example, in the publications U.S. Pat. No. 4,340,706, DE 37 13 601, DE 28 40 010 and WO 96/05234 A1, the corresponding disclosure of which is introduced herewith as reference.

The hydrogels obtained in the solution polymerization or the inverse suspension and emulsion polymerization in process step a) are at least partly dried in process step c).

In the case of solution polymerization in particular, however, it is preferable for the hydrogels first to be comminuted in an additional process step b) before the drying. This comminution is carried out by comminution devices known to the person skilled in the art, such as, for example, a meat chopper.

Drying of the hydrogel is preferably carried out in suitable dryers or ovens. Rotary tube ovens, fluidized bed dryers, plate dryers, paddle dryers or infrared dryers may be mentioned by way of example. It is furthermore preferable according to the invention for the drying of the hydrogel in process step c) to be carried out down to a water content of from 0.5 to 50 wt. %, preferably from 1 to 25 wt. %, particularly preferably 2 to 10 wt. %, the drying temperatures conventionally being in a range of from 100 to 200° C.

The at least partly dried water-absorbing polymer structures obtained in process step c) can also be ground in a further process step d), especially if they have been obtained by solution polymerization, and sieved off to the abovementioned desired particle size. Grinding of the dried water-absorbing polymer structures is preferably carried out in suitable mechanical comminution devices, such as, for example, a ball mill.

After the drying of the hydrogels and the optionally carried out further making up of the dried water-absorbing polymer structures, these can be modified in the surface region in a further process step e) (the surface post-crosslinking according to process step ii) described in still more detail in the following and the treatment with the compound of the structure I in process step iii) are excluded from the surface modification carried out in process step e)).

The preferred modification measure to be mentioned here is the bringing into contact of the outer region of the polymer structures with a compound containing $Al^{3+}$ ions before, during or after, preferably after the surface post-crosslinking according to process step iii). In this context it is preferable for the compound containing $Al^{3+}$ ions to be brought into contact with the water-absorbing polymer structures in an amount in a range of from 0.01 to 30 wt. %, particularly preferably in an amount in a range of from 0.05 to 20 wt. % and moreover preferably in an amount in a range of from 0.1 to 5 wt. %, in each case based on the weight of the water-absorbing polymer structures.

The outer region of the water-absorbing polymer structures is preferably brought into contact with the compound containing $Al^{3+}$ ions by mixing the polymer structure with the compound under dry conditions, or by bringing the polymer structures into contact with a fluid $F_1$ comprising a solvent, preferably water, water-miscible organic solvents, such as, for example, methanol or ethanol, or mixtures of at least two of these, and the compound containing $Al^{3+}$ ions, the components being brought into contact preferably by spraying the polymer particles with the fluid $F_1$ and mixing. In this connection, it is furthermore preferable for the polymer structures to be brought into contact with the fluid $F_1$ comprising the compound containing $Al^{3+}$ ions in a two-stage process. In this context, the two-stage process includes a first mixing operation, in which a large number of polymer structures are mixed with the fluid $F_1$, and a second mixing operation, in which the fluid $F_1$ is homogenized inside the polymer structures, the polymer structures being mixed in the first mixing operation at a speed such that the kinetic energy of the individual polymer structures on average is greater than the adhesion energy between the individual polymer structures, and the polymer structures being mixed thoroughly in the second mixing operation at a lower speed than in the first mixing operation.

By the treatment of the polymer structures with the fluid $F_1$ comprising the compound containing $Al^{3+}$ ions by the two-stage process described above, polymer structures having improved absorption properties can be obtained.

In this context, the fluid $F_1$ preferably comprises the compound containing $Al^{3+}$ ions, without taking into account water of crystallization, in an amount in a range of from 0.1 to 50 wt. %, particularly preferably in an amount in a range of from 1 to 30 wt. %, in each case based on the total weight of the fluid $F_1$. It is furthermore preferable for the fluid $F_1$ to be brought into contact with the polymer structures in an amount in a range of from 0.01 to 15 wt. %, particularly preferably in an amount in a range of from 0.05 to 6 wt. %, in each case based on the weight of the polymer structures.

Preferred compounds containing $Al^{3+}$ ions are $AlCl_3 \times 6H_2O$, $NaAl(SO_4)_2 \times 12H_2O$, $KAl(SO_4)_2 \times 12H_2O$, $Al_2(SO_4)_3 \times 14\text{-}18H_2O$ or aluminum lactate.

A further surface modification measure which may be mentioned at this point is that of bringing the water-absorbing polymer structures into contact with inorganic particles, for example with finely divided silicon dioxide, which is preferably applied in aqueous suspension, or with silica sol.

The modification measures carried out above in process step e), in particular the treatment with a compound containing $Al^{3+}$ ions, can in principle also be carried out while process steps ii) and iii) are being carried out, after process steps ii) and iii) have been carried out, after process step ii) has been carried out but before process step iii) has been carried out or after process step iii) has been carried out but before process step ii) has been carried out.

The surface post-crosslinking of the water-absorbing polymer structure, in which the water-absorbing polymer structure is first brought into contact with a surface post-crosslinking agent and is then heated, is carried out in process step ii). In this context, the post-crosslinking agent is preferably brought into contact with the polymer particles in the form of a fluid $F_2$ comprising the post-crosslinking agent and a solvent, especially if it is not liquid under the post-crosslinking conditions. Solvents which are employed in this context are preferably water, water-miscible organic solvents, such as, for example, methanol, ethanol, 1-propanol, 2-propanol or 1-butanol, or mixtures of at least two of these solvents, water being most preferred as the solvent. It is furthermore preferable for the fluid $F_2$ to comprise the post-crosslinking agent in an amount in a range of from 5 to 75 wt. %, particularly preferably 10 to 50 wt. %, and most preferably 15 to 40 wt. %, based on the total weight of the fluid $F_2$.

In the process according to the invention, the water-absorbing polymer structure is preferably brought into contact with the fluid $F_2$ comprising the post-crosslinking agent by thorough mixing of the fluid $F_2$ with the water-absorbing polymer structure.

Suitable mixing units for application of the fluid $F_2$ are, for example, the Patterson-Kelley mixer, DRAIS turbulence mixer, Lödige mixer, Rubergi mixer, screw mixers, plate mixers and fluidized bed mixers as well as continuously operating vertical mixers, in which the polymer structure is mixed by means of rotating blades in rapid frequency (Schugi mixer). Mixing devices in which mixing of the fluid $F_2$ with the water-absorbing polymer structure is carried out at least partly in a rotating container can also be employed. Such mixing devices are obtainable, for example, from Lindor, Dordrecht, Holland and are marketed, for example, under the product names Lindor 70, Lindor 200, Lindor 500, Lindor 750, Lindor 1000, Lindor 1500, Lindor 2000, Lindor 2300, Lindor 4000, Lindor 7000, Lindor 8000, Lindor 12000, Lindor 14000 or Lindor 25000.

In the process according to the invention, during the post-crosslinking the water-absorbing polymer structure is preferably brought into contact with at most 20 wt. %, particularly preferably with at most 15 wt. %, moreover preferably with at most 10 wt. %, moreover still more preferably with at most 5 wt. % of solvent, preferably water, and most preferably of all with less than 3 wt. %, in each case based on the weight of the water-absorbing polymer structure.

In the case of water-absorbing polymer structures in the form of preferably spherical particles, it is furthermore preferable according to the invention for the components to be brought into contact in a manner such that merely the outer region, but not the inner region of the particulate water-absorbing polymer structures is brought into contact with the fluid $F_2$ and therefore the post-crosslinking agent.

Compounds which have at least two functional groups which can react with functional groups of a polymer structure in a condensation reaction (=condensation crosslinking agents), in an addition reaction or in a ring-opening reaction, or polyvalent metal cations which render possible a crosslinking of the polymer structure by means of electrostatic interaction between the polyvalent metal cation and the functional groups of a polymer structure are preferably understood as post-crosslinking agents which are employed in the process according to the invention. Those post-crosslinking agents which have been mentioned as crosslinking agents of crosslinking agent classes II and IV in WO 2004/037903 A2 are preferred as post-crosslinking agents in the process according to the invention.

Among these compounds, particularly preferred post-crosslinking agents are condensation crosslinking agents, such as, for example, diethylene glycol, triethylene glycol, polyethylene glycol, glycerol, polyglycerol, propylene glycol, diethanolamine, triethanolamine, polyoxypropylene, oxyethylene-oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxolan-2-one.

After the water-absorbing polymer structures have been brought into contact with the post-crosslinking agent or with the fluid comprising the post-crosslinking agent they are heated to a temperature in the range of from 50 to 300° C., preferably 75 to 275° C. and particularly preferably 150 to 250° C., so that, preferably as a result of this, the outer region of the polymer structures is more highly crosslinked compared with the inner region (=post-crosslinking). The duration of the heat treatment is limited by the risk that the desired profile of properties of the water-absorbing polymer structures is destroyed as a result of the action of heat.

In process step iii) of the process according to the invention, the water-absorbing polymer structures are brought into contact with the compound of the structure I, wherein it is preferable for the radicals $R^1$, $R^2$, $R^3$, $R^4$ and $R^5$ to represent a hydrogen atom, the compound of the structure is consequently salicylic acid or a metal salt of salicylic acid, the use of salicylic acid, sodium salicylate and zinc salicylate being particularly preferred and the use of zinc salicylate being most preferred.

In this context it is particularly preferable for the compound of the structure I to be brought into contact with the water-absorbing polymer structures in an amount in a range of from 0.001 to 10 wt. %, particularly preferably in a range of from 0.05 to 5 wt. % and most preferably in an amount in a range of from 0.1 to 3 wt. %, in each case based on the total weight of the water-absorbing polymer structures.

According to a particularly preferred embodiment of the process according to the invention, the compound of the structure I is employed in the form of a powder comprising particles of the structure I, it furthermore being preferable for such a powder to comprise at most 25 wt. %, still more preferably at most 10 wt. %, moreover preferably at most 5 wt. %, in each case based on the total weight of the compound of the structure I, but most preferably no preferably individual particles which are greater than 700 µm, particularly preferably greater than 500 µm and most preferably greater than 300 µm in diameter. However, it is entirely possible for the powder of the compound I also to contain agglomerates of at least two particles which are greater than 700 µm, 500 µm or 300 µm, it being entirely possible for the amount of these agglomerates also to be greater than 25 wt. %, 10 wt. % or 5 wt. %. In particular, it may prove advantageous if the powder of the compound of the structure I is based to the extent of at least 50 wt. %, still more preferably to the extent of at least 90 wt. % and most preferably exclusively on particles having a diameter in a range of from 50 to 800 µm, particularly preferably 50 to 500 µm and most preferably 50 to 350 µm.

The water-absorbing polymer structures optionally already post-crosslinked on the surface are preferably brought into contact with the compound of the structure I by simple mixing of the two components, the compound of the structure I preferably being mixed in particulate form with the water-absorbing polymer structure. However, it is also conceivable in principle for the compound of the structure I to be mixed with the water-absorbing polymer structure in the form of a solution or a suspension, for example in the form of an aqueous solution. As already stated above, however, the mixing of the compound of the structure I in particulate form, in particular in the form of a powder, with the water-absorbing polymer structures has proved to be advantageous in particular.

Suitable mixing units for mixing of the compound of the structure I and the water-absorbing polymer structures are, for example, the Patterson-Kelley mixer, DRAIS turbulence mixer, Lödige mixer, Ruberg mixer, screw mixers, plate mixers and fluidized bed mixers as well as continuously operating vertical mixers, in which the polymer structure is mixed by means of rotating blades in rapid frequency (Schugi mixer). Here also, the use, already described in connection with the surface post-crosslinking, of mixing devices in which the mixing of the pulverulent compound of the structure I or of the solution containing the compound of the structure I with the water-absorbing polymer structures is carried out at least partly in a rotating container is conceivable.

After the water-absorbing polymer structures have been brought into contact with the compound of the structure I, the water-absorbing composition obtained in this way can be subjected to still further modification measures. The addition of the binders mentioned above in connection with the composition according to the invention is conceivable here in particular.

A contribution towards achieving the abovementioned objects is also made by a water-absorbing composition which is obtainable by the process according to the invention described above.

It is particularly preferable for the water-absorbing composition according to the invention described above and also the water-absorbing composition according to the invention obtainable by the process described above to have at least one of the following properties:

(β1) a retention, determined in accordance with ERT 441.2-02, of at least 20 g/g, preferably at least 25 g/g and particularly preferably in a range of from 25 to 50 g/g;

(β2) an absorption against a pressure of 0.7 psi (50 g/cm$^2$), determined (in the case of particles for the total particle size fraction) in accordance with ERT 442.2-02, of at least 15 g/g, particularly preferably of at least 20 g/g;

(β3) a degree of neutralization of at most 78 mol %, particularly preferably of at most 70 mol % and at least 50 mol %;

(β4) a flow rate, determined in accordance with ERT 450.2-02, of at least 9 g/sec, particularly preferably of at least 9.5 g/sec and most preferably of at least 10 g/sec;

(β5) a surface tension, determined in accordance with the test method described herein, of at least 60 mN/m, particularly preferably of at least 65 mN/m and most preferably of at least 70 mN/m.

A contribution towards achieving the abovementioned objects is also made by a composite comprising a water-absorbing composition according to the invention or a water-absorbing composition which is obtainable by the process according to the invention and a substrate.

In this context it is preferable for the water-absorbing composition according to the invention and the substrate to be firmly bonded to one another. Preferred substrates are films of polymers, such as, for example, of polyethylene, polypropylene or polyamide, metals, nonwovens, fluff, tissues, woven fabric, natural or synthetic fibers or other foams. It is furthermore preferable according to the invention for the composite to comprise at least one region which comprises the water-absorbing composition according to the invention in an amount in a range of from about 15 to 100 wt. %, preferably about 30 to 100 wt. %, particularly preferably from about 50 to 99.99 wt. %, furthermore preferably from about 60 to 99.99 wt. % and moreover preferably from about 70 to 99 wt. %, in each case based on the total weight of the region in question in the composite, this region preferably having a size of at least 0.01 cm³, preferably at least 0.1 cm³ and most preferably at least 0.5 cm³.

In one embodiment of the composite according to the invention, the composite is a flat composite such as is described as "absorbent material" in WO 02/056812 A1. The disclosure content of WO 02/056812 A1, in particular with respect to the exact structure of the composite, the weight of its constituents per unit area and its thickness, is introduced herewith as reference and represents a part of the disclosure of the present invention.

A further contribution towards achieving the abovementioned objects is made by a process for the production of a composite, wherein the water-absorbing composition according to the invention or the water-absorbing composition obtainable by the process according to the invention and a substrate and optionally an additive are brought into contact with one another. Substrates which are preferably employed are those substrates which have already been mentioned above in connection with the composite according to the invention.

A contribution towards achieving the abovementioned objects is also made by a composite obtainable by the process described above, this composite preferably having the same properties as the composite according to the invention described above.

According to another aspect of the present invention, the composite is constructed as a hygiene article core which comprises, in each case based on the hygiene article core, at least 30 wt. %, preferably at least 50 wt. % and moreover preferably at least 70 wt. % of the water-absorbing composition according to the invention and at least 1 wt. %, preferably at least 5 wt. % and moreover preferably at least 10 wt. % of the substrate and optionally also further conventional auxiliaries and/or adhesives, wherein the sum of the percentages by weight of the individual components contained in the hygiene article core gives 100 wt. %. Materials which serve to fix the superabsorbent composition according to the invention, which is usually in the form of particles, are particularly preferred as the substrate in connection with the hygiene article core. These can be fibers or knitted fabrics or woven fabrics as well as nets. It is furthermore possible for the water-absorbing composition, which, for example, is in the form of a powder and therefore particulate, to be bonded to the substrate by an adhesive, such as a glue. The substrate being configured such that the water-absorbing composition is accommodated in a recess of the substrate likewise corresponds to one embodiment. Conventional auxiliaries which can likewise be incorporated into the hygiene article core are, for example, substances, cosmetic substances, which increase skin tolerability, disinfectants, antimicrobial substances and the like.

In a further aspect, the present invention relates to hygiene articles comprising an upper layer which is permeable to liquid, a lower layer which is impermeable to liquid and a composite according to the invention arranged between the upper layer and the lower layer. Possible hygiene articles are both feminine hygiene articles and adult incontinence products, and nappies for infants, babies and small children. It is preferable for the hygiene article to comprise a hygiene article core described above. All those woven fabrics, laid fabrics and knitted layers, which are usually made of celluloses or cellulose derivatives and are optionally bonded with plastics, such as polypropylene or polyethylene, and which are known and seem suitable to the person skilled in the art for this purpose are in principle possible as the upper layer which is permeable to liquid. The nonwovens which are usually likewise made of a cellulose or cellulose derivative laid fabric, knitted fabric or stitched fabric and which are familiar to the person skilled in the art in the industry are also employed as the lower layer which is impermeable to liquid, these nonwovens in general being sealed with a layer of plastic, usually of polypropylene or polyethylene.

A further contribution towards achieving the abovementioned objects is made by chemical products comprising the water-absorbing compositions according to the invention or a composite according to the invention. Preferred chemical products are, in particular, foams, shaped articles, fibers, foils, films, cables, sealing materials, liquid-absorbing hygiene articles, in particular nappies and sanitary towels, carriers for plant or fungal growth-regulating agents or plant protection active compounds, additives for building materials, packaging materials or soil additives.

The use of the water-absorbing composition according to the invention or of the composite according to the invention in chemical products, preferably in the abovementioned chemical products, in particular in hygiene articles, such as nappies or sanitary towels, and the use of the superabsorber particles as carriers for plant or fungal growth-regulating agents or plant protection active compounds also make a contribution towards achieving the abovementioned objects. For the use as a carrier for plant or fungal growth-regulating agents or plant protection active compounds it is preferable for it to be possible for the plant or fungal growth-regulating agents or plant protection active compounds to be released over a period of time controlled by the carrier.

A contribution towards achieving the abovementioned objects is furthermore made by the use of a compound of the structure I

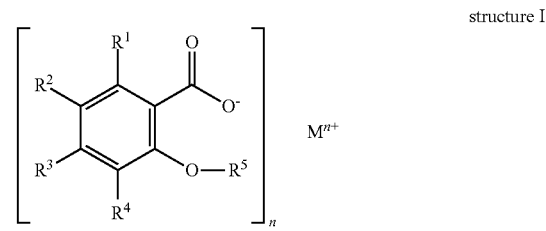

structure I in which $R^1$, $R^2$, $R^3$ and $R^4$ can be identical or different and in each case represent a hydrogen atom, a halogen atom, for example a chlorine atom or a bromine atom, a $C_1$- to $C_4$-hydrocarbon group, preferably a methyl group or an ethyl group, particularly preferably a methyl group, or a hydroxyl group, $R^5$ represents a hydrogen atom, a $C_1$- to $C_4$-hydrocarbon group or an acetyl group, preferably a hydrogen atom or an acetyl group and most preferably a hydrogen atom, n represents an integer chosen from the group consisting of 1, 2 or 3, particularly preferably the number 1 or the number 2 and most preferably the number 2, and $M^{n+}$ represents an n-valent metal cation or an $H^+$ cation, preferably an $H^+$ cation, a monovalent metal cation of an alkali metal or a divalent metal cation of an alkaline earth metal or of a transition metal, particularly preferably an $H^+$ cation, an $Na^+$ cation or a divalent metal cation of a transition metal of groups 10, 11 or 12, particularly preferably of group 12 and most preferably a $Zn^{2+}$ cation, but in particular the use of salicylic acid, sodium salicylate or zinc salicylate and most preferably the use of zinc salicylate, for improving the odor-binding properties of water-absorbing polymer structures.

The invention is explained in more detail below with the aid of test methods and non-limiting figures and examples.

FIG. 1 shows the odor-binding effect of the use according to the invention of zinc salicylate in the case of a superabsorber having a degree of neutralization of 55 mol % and in the case of a superabsorber having a degree of neutralization of 75 mol %.

TEST METHODS

General

Unless other test methods are given in the following, the test methods which are generally known to the person skilled in the art and appear to be conventional are used, test methods of EDANA (European Diaper and Nonwoven Association), which are generally described as "ERT methods", being used in particular.

Determination of the Surface Tension

In the determination of the surface tension, the extent to which a particular amount of water-absorbing composition which has been suspended under defined conditions in a defined amount of 0.9 wt. % strength NaCl solution influences the surface tension of this aqueous solution is analyzed. If the surface tension is greatly reduced by the odor-binding substance, the problem of "rewets" may occur when the water-absorbing composition is employed in hygiene articles. A "rewet" leads to body fluids, such as, for example, urine, which have already been absorbed by the hygiene article being released again, for example under the action of an external pressure.

All the solutions employed for determination of the surface tension are temperature-controlled at 23° C. Before the determination, all the apparatuses are rinsed adequately with distilled water, degreased with isopropanol and dried briefly over a Bunsen burner with a blue flame.

The surface tension is determined by means of the ring method using the K8 interfacial tensiometer (Krüss GmbH, Hamburg). In this procedure, a platinum ring connected to a weighing system is immersed in the NaCl solution and then pulled out again slowly, the force needed to pull the ring out of the liquid against the interfacial tension being determined.

a) Construction of the Measurement Apparatus

A torsion wire is tensioned between 2 clamping pieces. Via a worm gear, torsion can be exerted on the wire and the tensiometer in the rear part of the apparatus can be adjusted. The gearing in the front part is permanently connected to a nonius scale. The value of the interfacial tension can be read off directly on this scale in mN/m. The balance arm is clamped on the torsion wire at an angle of 90°. The measuring body is pushed with its pin into a ring recess in the torsion balance on the lower end of the vertical arm. The measuring body must be completely flat on its under-side, so that simultaneous application of the forces at all points is possible. By twisting the torsion wire, the measuring body is deflected out of the zero position; the ring is raised or lowered. The vertical movement of the balance arm is displayed on a dark screen via a lens system.

b) Preparation for the Measurement

After the torsion balance has been stopped by the screw, the pin of the ring is pushed into the ring recess in the balance. The vessel for the liquid is cleaned by means of chromic-sulphuric acid, boiled up in distilled water for a relatively long time and then flamed briefly with a peaked Bunsen burner flame before use. The liquid to be analyzed (25 ml) is poured into the cooled glass dish and placed in the thermostatically controlled vessel. There should be a distance of 2 cm between this and the table. This distance is adjusted by means of the micrometer screw. Before each measurement, the circular scale is to be set at 0 with the screw. The lamp is to be switched on with the switch. After releasing the stop, the luminous pointer should level out on the central line of the dark screen. If this is not the case, the zero position is readjusted by turning the screw on the rear of the head part. In this state the balance swings freely around its zero position. The instrument is now ready for measurement.

c) Measurement of the Surface Tension

The thermostatically controlled table is raised with the hand wheel until the ring is completely covered with liquid. The table is carefully lowered with the hand wheel until the luminous pointer is deflected out of the zero position due to the interfacial tension acting on the ring. By turning the screw anticlockwise, the torsion of the band is increased and tension is exerted on the ring. During this, the luminous pointer which can be observed on the dark screen scale is displaced upwards. Using the micrometer screw, the luminous pointer is brought back to the zero position by lowering the measuring vessel. The alternate careful increase in tension and subsequent lowering of the measuring vessel is repeated until the tension applied to the ring completely overcomes the interfacial tension forces and tears the ring upwards out of the surface. The interfacial tension is read off in 0.1 mN/m on the nonius scale.

d) Calibration

The K8 tensiometer is calibrated with doubly distilled water at 20° C.=72.6 mN/m. Should another value result, a correction FIGURE is used. For example, if 73.0 mN/m is measured for water at 20° C. instead of 72.6 mN/m, the correction factor is equal to the quotient of the theoretical value and the value read off.

$$72.6/73=0.994$$

The values read off are to be multiplied by such a correction factor.

e) Sample Preparation 150 g of 0.9% strength NaCl solution are initially introduced into a 250 ml glass beaker and stirred with a magnetic stirrer (200 rpm). 2 g of the product to be tested are sprinkled slowly into the spout formed in the 0.9% strength NaCl solution. When sprinkling in is complete, the solution is stirred for 3 minutes. The solution is then left to stand for 15 minutes. 25 ml of this solution are introduced into the sample vessel of the K8 tensiometer using a pipette and the surface tension is measured 5 minutes later. 3 measurements are performed.

EXAMPLES

Example 1a

Provision of a Water-Absorbing Polymer Structure (Process Step i))

A monomer solution comprising 300 g of acrylic acid, which was neutralized to the extent of 75 mol % with sodium hydroxide solution, 441 g of water, 0.9 g of polyethylene glycol 300 diacrylate and 1.35 g of allyloxypolyethylene glycol acrylate was freed from dissolved oxygen by flushing with nitrogen and cooled to the start temperature of 4° C. When the start temperature was reached, the initiator solution (0.3 g of sodium peroxydisulphate in 10 g of $H_2O$, 0.07 g of 35% strength hydrogen peroxide solution in 10 g of $H_2O$ and 0.015 g of ascorbic acid in 2 g of $H_2O$) was added. When the end temperature of approx. 100° C. was reached, the gel formed was chopped such that granules with particles of about 1 to 3 mm in size were obtained. The water content was approx. 50%. These particles were dried at 150° C. for 120 minutes. The dried polymer was coarsely crushed, ground, and sieved to a powder having a particle size of from 150 to 850 μm (powder A).

Example 2a

Surface Post-Crosslinking of a Water-Absorbing Polymer Structure (Process Step ii))

For the post-crosslinking, 100 g of powder A obtained above were mixed with a solution of 1 g of 1,3-dioxolan-2-one and 3 g of water, with vigorous stirring, and the mixture was then heated for 30 minutes in an oven temperature-controlled at 180° C. A water-absorbing polymer structure post-crosslinked on the surface (powder B) was obtained.

Example 1b

Provision of a Water-Absorbing Polymer Structure (Process Step i))

A monomer solution comprising 300 g of acrylic acid, which was neutralized to the extent of 55 mol % with sodium hydroxide solution, 491 g of water, 0.9 g of polyethylene glycol 300 diacrylate and 1.35 g of allyloxypolyethylene glycol acrylate was freed from dissolved oxygen by flushing with nitrogen and cooled to the start temperature of 4° C. When the start temperature was reached, the initiator solution (0.3 g of sodium peroxydisulphate in 10 g of $H_2O$, 0.07 g of 35% strength hydrogen peroxide solution in 10 g of $H_2O$ and 0.015 g of ascorbic acid in 2 g of $H_2O$) was added. When the end temperature of approx. 100° C. was reached, the gel formed was chopped such that granules with particles of about 1 to 3 mm in size were obtained. The water content was approx. 50%. These particles were dried at 150° C. for 120 minutes. The dried polymer was coarsely crushed, ground, and sieved to a powder having a particle size of from 150 to 850 μm (powder C).

Example 2b

Surface Post-Crosslinking of a Water-Absorbing Polymer Structure (Process Step ii))

For the post-crosslinking, 100 g of powder C obtained above were mixed with a solution of 1 g of 1,3-dioxolan-2-one and 3 g of water, with vigorous stirring, and the mixture was then heated for 30 minutes in an oven temperature-controlled at 180° C. A water-absorbing polymer structure post-crosslinked on the surface (powder D) was obtained.

Example 3

Bringing a Water-Absorbing Polymer Structure into Contact with Zinc Salicylate (Process Step iii))

The water-absorbing polymer structure post-crosslinked on the surface obtained in Example 2a (powder B) was mixed with various amounts of zinc salicylate powder (obtained from Vertellus Specialties Inc., Indianapolis, USA) (see the data in the following Table 1). The compositions according to the invention according to powders E and F were thereby obtained:

As a further comparison, the water-absorbing polymer structure post-crosslinked on the surface obtained in Example 2a (powder B) was also after-treated with zinc ricinoleate (powder G).

TABLE 1

|  | Powder B (comparison) | Powder E | Powder F | Powder G (comparison) |
|---|---|---|---|---|
| Amount of zinc compound added [wt. %] | 0 | 1 | 3 | 1 |
| TB [g/g] | 34.0 | 34.1 | 32.2 | 31.3 |
| $AAP_{0.7psi}$ [g/g] | 20.5 | 20.7 | 20.6 | 18.7 |
| Flow rate | 11 | 11 | 10.6 | 10.4 |
| Surface tension [mN/m] | 64.2 | 62.7 | 63.6 | 47.8 |

The water-absorbing polymer structure post-crosslinked on the surface obtained in Example 2b (powder D) was furthermore mixed with various amounts of zinc salicylate powder (see the data in the following Table 2). The compositions according to the invention according to powders H and I were thereby obtained.

As a further comparison, the water-absorbing polymer structure post-crosslinked on the surface obtained in Example 2b (powder D) was also after-treated with zinc ricinoleate (powder J) and with 5 wt. % of Tegosorb® A30 solution (contains 15 wt. % of zinc ricinoleate, powder K).

TABLE 2

|  | Powder D (comp.) | Powder H | Powder I | Powder J (comp.) | Powder K (comp.) |
|---|---|---|---|---|---|
| Amount of zinc compound added [wt. %] | 0 | 0.5 | 1 | 1 | 0.75[1] |
| TB [g/g] | 30.3 | 30 | 30.5 | 29.6 | 29.0 |
| $AAP_{0.7psi}$ [g/g] | 21.1 | 19.9 | 20.4 | 20.6 | 18.9 |
| Flow rate | 10.2 | n.d. | n.d. | 10.0 | 6.9 |
| Surface tension [mN/m] | 71.1 | 71 | 71.1 | 45.9 | 41.5 |

[1] 5 wt. % of a Tegosorb ® A30 solution which contains 15 wt. % of zinc ricinoleate was applied.

It can be seen from the results of Tables 1 and 2 that the addition according to the invention of the zinc salicylate does not adversely influence the absorption properties of the water-absorbing polymer structures.

Example 4

Determination of the Odor-Binding Properties of the Compositions According to The Invention The odor-binding properties of powders B, D, E, G, H, I, J and K were determined.

The odor-binding properties of the compositions according to the invention were determined via determination of the release of ammonia by the water-absorbing composition.

For this, *Proteus mirabilis* cells were cultured overnight on CASO slant agar at 37° C. Each tube was washed off with 5 ml of synthetic urine. The bacteria suspension was adjusted to a germ content of approximately $10^5$ CFU/ml (CFU=colony-forming units) with synthetic urine and 1 g/l of meat extract and 1 g/l of peptone.

33 ml of the synthetic urine which contained 1 g/l of meat extract and 1 g/l of peptone and to which bacteria had been added were added to 1 g portions of the water-absorbing composition. On the one hand a batch without a composition according to the invention and a water-absorbing composition without zinc salicylate were employed as a control.

The vessels were closed with a rubber stopper, through the bore of which a Dräger diffusion tube was led, and incubated in an incubating cabinet at 37° C. The ammonia released was measured in ppm×h. The initial germ count (measured in CFU) of the urine was determined by plating out suitable dilutions on nutrient media plates. For the release of ammonia, the mean of two batches was calculated.

The odor-binding properties of powders E, H and I according to the invention and of the comparison products B, D, G, J and K can be seen in FIG. 1. It can be seen from this FIGURE that in particular the combination of a water-absorbing polymer structure partly neutralized to the extent of only 55 mol % together with 1 wt. % of zinc salicylate leads to a water-absorbing composition which releases no ammonia even after 17 hours. It can furthermore be seen from FIG. 1 that an amount used of 0.5 wt. % of zinc salicylate leads to a longer delay in the release of ammonia than a use of 1 wt. % of zinc ricinoleate. An amount used of 0.5 wt. % of zinc salicylate also leads to a delay in the release of ammonia which is comparable to the delay with the use of 0.75 wt. % of zinc ricinoleate, which was applied in the form of the Tegosorb A30 dispersion. Zinc salicylate can consequently be employed in smaller amounts compared with the zinc ricinoleate known from the prior art.

The invention claimed is:

1. A water-absorbing particulate composition comprising (a) water-absorbing polymer particulate structure wherein the water-absorbing polymer comprises partly neutralized, crosslinked sodium polyacrylate comprising from 0.01 to 2.5 wt % of one or more crosslinking agents based on the weight of the water-absorbent polymer wherein the sodium polyacrylate is neutralized to from 50 to 60 mol %, (b) a surface crosslinking agent wherein the water-absorbing polymer particulate structures have an inner region and an outer region surrounding the inner region, the outer region having a higher degree of crosslinking than the inner region due to the surface crosslinking agent, (c) 1 wt % of zinc salicylate in the form of a powder and (d) a binder to attach and immobilize the zinc salicylate to the surface of the water-absorbing particulate composition wherein the binder is selected from thermoplastic hot melt adhesives, hydrophilic water-soluble polymer or water, and wherein the water-absorbing particulate composition have an average particle size according to ERT-420.2.02 of from 150 µm to 600 µm and the water-absorbing particulate composition comprises at least 75 wt % of the particles, based on the total weight of the water-absorbing particulate composition, have a particle size in the range of 300 to 600 µm and wherein the water-absorbing particulate composition has (β1) a retention determined according to ERT 441.2-02 of from 25 g/g to 50 g/g; and (β2) an absorption (determined for the entire particle size fraction in the case of particles) against a pressure of 0.7 psi (50 g/cm$^2$) to ERT 442.2-02 of at least 15 g/g; wherein the water-absorbing particulate composition has an odor-binding effect of delay of release of ammonia of at least 17 hours and a surface tension of at least 60 mN/m.

2. The water-absorbing composition according to claim 1, wherein the internal crosslinking agent is selected from N,N'-methylenebisacrylamide, polyethylene glycol di(meth)acrylates, triallylmethylammonium chloride, tetraallylammonium chloride, allylnonaethylene glycol acrylate prepared with 9 mol of ethylene oxide per mol of acrylic acid, polyethylene glycol 300 diacrylate or allyloxypolyethylene glycol acrylate.

3. The water-absorbing composition according to claim 2, wherein the internal crosslinking agent is selected from polyethylene glycol 300 diacrylate or allyloxypolyethylene glycol acrylate.

4. The water-absorbing composition according to claim 2, wherein the post-crosslinking agent is selected from diethylene glycol, triethylene glycol, polyethylene glycol, glycerol, polyglycerol, propylene glycol, diethanolamine, triethanolamine, polyoxypropylene, oxyethylene-oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxolan-2-one.

5. The water-absorbing composition according to claim 1, wherein the zinc salicylate is contacted with the water-absorbing polymer structures in an amount within a range from about 0.1 to about 5% by weight, based on the total weight of the water-absorbing polymer structures.

6. The water-absorbing composition according to claim 1, wherein the post-crosslinking agent is selected from 1,3-dioxolan-2-one.

7. A composite comprising a water-absorbing composition according to claim 1, and a substrate.

8. A liquid-absorbing hygiene article comprising the water-absorbing composition according to claim 1.

9. A water-absorbing composition particulate obtainable by a process comprising the process steps of:
  i) providing a water-absorbing polymer particulate structure comprising partly neutralized crosslinked sodium polyacrylate comprising from 0.01 to 2.5 wt % of one or more crosslinking agents based on the weight of the water-absorbent polymer wherein the internal crosslinking agent is selected from N,N'-methylenebisacrylamide, polyethylene glycol di(meth)acrylates, triallylmethylammonium chloride, tetraallylammonium chloride, allylnonaethylene glycol acrylate prepared with 9 mol of ethylene oxide per mol of acrylic acid, polyethylene glycol 300 diacrylate or allyloxypolyethylene glycol acrylate and wherein the sodium polyacrylate is neutralized to from 50 to 60 mol %;
  ii) postcrosslinking the water-absorbing polymer structure with a surface crosslinking agent wherein the water-absorbing polymer structures have an inner region and an outer region surrounding the inner region, the outer region having a higher degree of crosslinking than the inner region due to the surface crosslinking agent;
  iii) contacting the surface crosslinked water-absorbing polymer structure of step ii) with a binder and 1 wt % of zinc salicylate in the form of a powder wherein the binder attaches and immobilize the zinc salicylate to the surface of the water-absorbing particulate composition wherein the binder is selected from thermoplastic hot melt adhesives, hydrophilic water-soluble polymer or water, and wherein process step iii) can be performed before, during or after process step ii) wherein the water-absorbing particulate composition have an average particle size according to ERT-420.2.02 of from 150 µm to 600 µm and the water-absorbing particulate composition comprises at least 75 wt % of the particles, based on the total weight of the water-absorbing particulate composition, have a particle size in the range of 300 to 600 µm and wherein the water-absorbing particulate composition has (β1) a retention determined to ERT 441.2-02 of from 25 g/g to 50 g/g; and (β2) an absorption (determined for the entire particle size fraction in the case of particles) against a pressure of 0.7 psi (50 g/cm$^2$) to ERT 442.2-02 of at least 15 g/g; wherein the water-absorbing particulate composition has an odor-binding effect of delay of release of ammonia of at least 17 hours and a surface tension of at least 60 mN/m.

10. A process for producing a water-absorbing particulate composition, comprising the process steps of:
   i) providing a water-absorbing polymer particulate structure wherein the water-absorbing polymer comprises partly neutralized, crosslinked sodium polyacrylate comprising from 0.01 to 2.5 wt % of one or more crosslinking agents based on the weight of the water-absorbent polymer wherein the sodium polyacrylate is neutralized to from 50 to 60 mol %;
   ii) postcrosslinking the water-absorbing polymer particulate structure with a surface crosslinking agent wherein the water-absorbing polymer structures have an inner region and an outer region surrounding the inner region, the outer region having a higher degree of crosslinking than the inner region due to the surface crosslinking agent;
   iii) contacting the water-absorbing polymer particulate structure with a binder and 1 wt % of zinc salicylate in the form of a powder wherein the binder attaches and immobilize the zinc salicylate to the surface of the water-absorbing particulate composition wherein the binder is selected from thermoplastic hot melt adhesives, hydrophilic water-soluble polymer or water, and wherein process step iii) can be performed before, during or after process step ii) wherein the water-absorbing particulate composition have an average particle size according to ERT-420.2.02 of from 150 µm to 600 µm and the water-absorbing particulate composition comprises at least 75 wt % of the particles, based on the total weight of the water-absorbing particulate composition, have a particle size in the range of 300 to 600 µm and wherein the water-absorbing particulate composition has (β1) a retention determined to ERT 441.2-02 of from 25 g/g to 50 g/g; and (β2) an absorption (determined for the entire particle size fraction in the case of particles) against a pressure of 0.7 psi (50 g/cm$^2$) to ERT 442.2-02 of at least 15 g/g; wherein the water-absorbing particulate composition has an odor-binding effect of delay of release of ammonia of at least 17 hours and a surface tension of at least 60 mN/m.

11. The process according to claim 10, wherein the internal crosslinking agent is selected from N,N'-methylenebisacrylamide, polyethylene glycol di(meth)acrylates, triallylmethylammonium chloride, tetraallylammonium chloride, allylnonaethylene glycol acrylate prepared with 9 mol of ethylene oxide per mol of acrylic acid, polyethylene glycol 300 diacrylate or allyloxypolyethylene glycol acrylate.

12. The process according to claim 10, wherein the internal crosslinking agent is selected from polyethylene glycol 300 diacrylate or allyloxypolyethylene glycol acrylate.

13. The process according to claim 10, wherein the-postcrosslinking agent is selected from diethylene glycol, triethylene glycol, polyethylene glycol, glycerol, polyglycerol, propylene glycol, diethanolamine, triethanolamine, polyoxypropylene, oxyethylene-oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxolan-2-one.

* * * * *